United States Patent [19]

Bjorkquist et al.

[11] Patent Number: 5,488,157

[45] Date of Patent: Jan. 30, 1996

[54] β-AMINOALKYL AND β-N-PEPTIDYLAMINOALKYL BORONIC ACIDS

[75] Inventors: David W. Bjorkquist, Wyoming; Rajan K. Panandiker, West Chester, both of Ohio

[73] Assignee: The Procter & Gamble Company, Cincinnati, Ohio

[21] Appl. No.: 434,901

[22] Filed: May 4, 1995

Related U.S. Application Data

[62] Division of Ser. No. 931,809, Aug. 14, 1992, Pat. No. 5,442,100.

[51] Int. Cl.⁶ ............................................. C07F 5/02
[52] U.S. Cl. .................... 562/7; 252/142; 252/542; 252/544; 252/545; 252/546
[58] Field of Search ................... 252/546, 542, 252/142, 544, 545, 546; 562/7; 569/8

[56] References Cited

U.S. PATENT DOCUMENTS 4,664,839  5/1987  Rieck ............................... 252/175

Primary Examiner—Richard L. Raymond
Attorney, Agent, or Firm—Goerge W. Allen

[57] ABSTRACT

A compound having the formula:

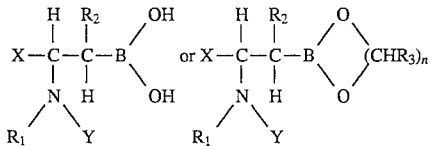

where $R_1$, $R_2$, and $R_3$ are independently hydrogen or $C_1-C_4$ alkyl; n is 2–4; X is aryl, substituted aryl or $C_1-C_6$ alkyl; Y is selected from the group consisting of hydrogen, amino acid, dipeptide or tripeptide linked through the C-terminal carboxylic acid, and amine protecting group is presented.

10 Claims, No Drawings

β-AMINOALKYL AND β-N-PEPTIDYLAMINOALKYL BORONIC ACIDS

This is a division of application Ser. No. 07/931,809, filed on Aug. 14, 1992 now U.S. Pat. No. 5,442,100.

FIELD OF THE INVENTION

This invention relates to a compound having the formula:

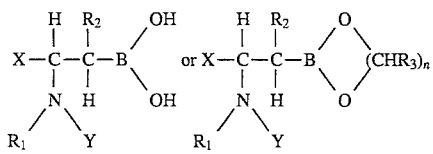

where $R_1$, $R_2$, and $R_3$ are independently hydrogen or $C_1$–$C_4$ alkyl; n is 2–4; X is aryl, substituted aryl or $C_1$–$C_6$ alkyl; Y is selected from the group consisting of hydrogen, amino acid, dipeptide or tripeptide linked through the C-terminal carboxylic acid, and amine protecting group.

BACKGROUND OF THE INVENTION

Protease-containing liquid detergent compositions are well known. A commonly encountered problem, particularly with heavy duty liquid laundry detergents, is the degradation by protease enzyme of second enzymes in the composition, such as lipase, amylase and cellulase. The performance of the second enzyme upon storage and its stability in product are thus impaired by the presence of protease in the liquid detergent product.

Boronic acids are known to reversibly inhibit protease. This inhibition of protease by boronic acid is reversible upon dilution, as occurs in wash water.

It is difficult to find an effective reversible protease inhibitor which is stable over time in a liquid detergent product. A search for a boronic acid which is a good reversible serine protease inhibitor and does not lose efficacy in product over time has now led to the synthesis of a novel compound of the structure described below. A new method for synthesizing β-aminoalkyl and β-N-peptidylaminoalkylboronic acids is also described below. Lastly, a new use for the subject compound or its derivatives as an effective serine protease inhibitor in a liquid detergent composition containing serine protease is described below.

Certain boronic acids are cited as subtilisin inhibitors in Phillip, M. and Bender, M. L., "Kinetics of Subtilisin and Thiosubtilisin", *Molecular & Cellular Biochemistry*, vol. 51, pp. 5–32 (1983), and in Phillip, M. and S. Maripuri, "Inhibition of Subtilisin by Substituted Arylboronic Acids", *FEBS Letters*, vol. 133(1), pp. 36–38 (October, 1981). Many of these inhibitors, however, are arylboronic acids, which owing to protodeboronation may not be stable under the slightly alkaline conditions found in many liquid detergents. It is believed that alkylboronic acids, particularly those with atoms other than hydrogen on the α carbon, may not possess the desired stability due to autoxidation as discussed by Johnson, J., Van Campen, M., and Grummitt, O., *Journal of the American Chemical Society*, vol. 60, 111–115 (1938).

Known synthetic routes to prepare boronic acid compounds have been reviewed by D. Matteson in *The Chemistry of the Metal Carbon Bond*, vol. 4, chapter 3, pp. 307–409, edited by F. Hartley (1987) and in *Tetrahedron*, vol. 45, pp. 1859–1885 (1989). Most of the references cited in Matteson's review articles and in the review on the use of catecholborane by C. Lane and G. Kabalka, *Tetrahedron*, vol. 32, pp. 981–990 (1976) are to the hydroboronation of olefins that lack heteroatom substitution. Only one reference could be found which is relevant to the formation of a boronic acid possessing the nitrogen heteroatom two carbons removed (i.e. β) from boron: Butler, D. and Soloway, A., *Journal of the American Chemical Society*, vol. 88, pp. 484–487 (1966). These authors demonstrated that it was possible to form β-ureidoethyl and β-carbamidoehylboronic acids from the corresponding N-vinyl urethan, and N-vinyl urea in three steps by hydroboration with borane followed by oxidation and hydrolysis. Later, Dicko, A., Montruy, M., and Baboulene, M. published on the formation of γ-aminoboronic acids in *Synthesis Communications*, vol. 18, pp. 459–463 (1988). Synthesis of α-N-peptidylaminoboronic acids is described in EP 0293-881, Kettner, published Dec. 7, 1988.

The novel compounds and method of synthesis herein have not yet been described, nor have liquid laundry detergents containing them.

SUMMARY OF THE INVENTION

The present invention relates to a compound having the following structure:

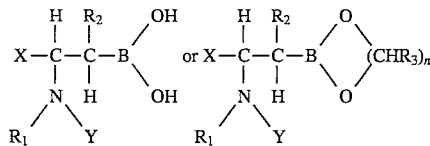

where $R_1$, $R_2$, and $R_3$ are independently hydrogen or $C_1$–$C_4$ alkyl; n is 2–4; X is aryl, substituted aryl or $C_1$–$C_6$ alkyl; and Y is selected from the group consisting of hydrogen, amine protecting group and amino acid, dipeptide or tripeptide linked through the C-terminal carboxylic acid.

DESCRIPTION OF THE INVENTION

The Compounds

The compounds herein have the structure:

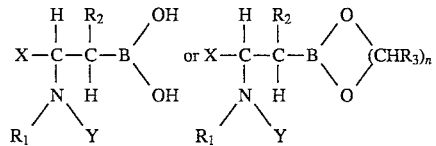

where $R_1$, $R_2$, and $R_3$ are independently hydrogen or $C_1$–$C_4$ alkyl; n is 2–4; X is aryl, substituted aryl or $C_1$–$C_6$ alkyl; Y is selected from the group consisting of hydrogen, amine protecting group and amino acid, dipeptide or tripeptide linked through the C-terminal carboxylic acid. Suitable amine protecting groups are described in *Protecting Groups in Organic Synthesis*, by T. W. Greene and P. G. M. Wuts, pp. 309–405, which is incorporated herein by reference. For example, these could include (in order of preference) any one of the following:

-continued

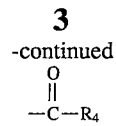

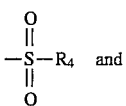

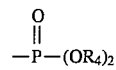

where $R_4$ is $C_1$–$C_4$ alkyl, aryl, or substituted aryl. Compounds named β-aminoalkylboronic acid or β-N-peptidylaminoalkylboronic acid or β-aminoalkylboronate ester or β-N-peptidylaminoalkylboronate ester are described herein.

Preferred compounds have the following formula:

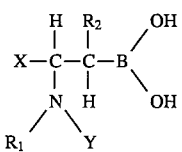

where $R_1$ and $R_2$ are independently hydrogen or methyl; X is aryl, substituted aryl, or $C_1$–$C_4$ alkyl; and Y is an amine protecting group selected from the group consisting of t-butoxycarbonyl (BOC), methoxycarbonyl or benzyloxycarbonyl (CBZ), and

where $R_5$ is phenyl, substituted phenyl or $C_1$–$C_4$ alkyl.

Another preferred compound has the same formula as the above, except that Y is

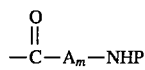

where A is independently selected from naturally occurring amino acids, m=1–3, and P is hydrogen or an amine protecting group selected from the group consisting of t-butoxycarbonyl (BOC), methoxycarbonyl, or benzyloxycarbonyl (CBZ), and

where $R_5$ is phenyl, substituted phenyl or $C_1$–$C_4$ alkyl.

Twenty suitable naturally occurring amino acids are listed in *Biochemistry* by Lehninger, pp. 73–79 (1981).

More preferred compounds are

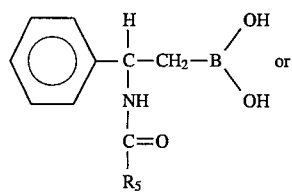

-continued

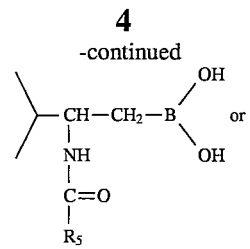

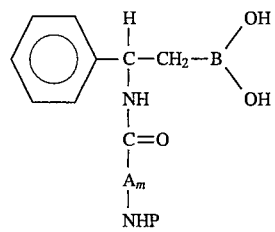

where m=1–3; A is independently selected from the group consisting of alanine, valine, leucine, isoleucine, phenylalanine, glycine, and threonine; and P is selected from:

Most preferred are:

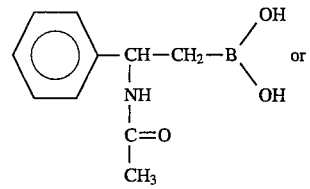

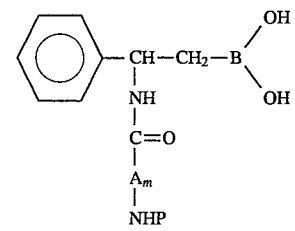

where m=1–3; A is independently selected from the group consisting of alanine, glycine, leucine, valine and phenylalanine; and P is selected from the group consisting of t-butoxycarbonyl, methoxycarbonyl, benzyloxycarbonyl; and

Also described herein is a new composition of matter having serine protease reversible inhibition properties, comprising the compound described herein and serine protease (described below).

Also described herein is a composition for use as an effective reversible serine protease inhibitor which comprises as an essential ingredient β-aminoalkylboronic acid or β-N-peptidylaminoalkylboronic acid in a liquid medium.

Also described herein is a method of reversibly inhibiting serine protease including the steps of:

(a) mixing from about 0.0001 to about 10 weight % of β-aminoalkylboronic acid or β-N-peptidylaminoalkylboronic acid in a liquid medium; and (b) mixing into the same liquid medium from about 0.0001 to about 10 weight % of active enzyme of serine protease.

Included herein is a method of reversibly inhibiting serine protease including the steps of:

(a) mixing from about 0.0001 to about 10 weight % of the compound described herein in a liquid medium; and (b) mixing into the same liquid medium from about 0.0001 to about 10 weight % of active enzyme of serine protease.

Synthesis of β-Aminoalkylboronic Acid

This invention describes a process for synthesizing β-aminoalkylboronic acid, comprising the steps of:

(a) reacting dihaloborane dimethyl sulfide complex and substituted silylated enamine under positive inert gas pressure to form β-silylaminoalkyldihaloborane; and hydrolyzing the β-silylaminoalkyldihaloborane to form β-aminoalkylboronic acid hydrohalide salt; and (b) neutralizing the β-aminoalkylboronic acid hydrohalide salt to form β-aminoalkylboronic acid.

Included herein is a process for synthesizing a compound of the formula:

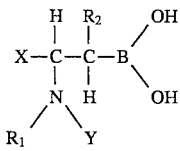

where $R_1$ and $R_2$ are independently hydrogens or $C_1$–$C_4$ alkyls; and X is aryl, substituted aryl or $C_1$–$C_6$ alkyl. Preferably, $R_1$ and $R_2$ are hydrogen and X is aryl or substituted aryl.

This invention also includes a process for synthesizing β-aminoalkylboronate ester, comprising the steps of:

(a) reacting dihaloborane dimethyl sulfide complex and substituted silylated enamine under positive inert gas pressure to form β-silylaminoalkyldihaloborane; and then reacting the β-silylaminoalkyldihaloborane with a diol to form β-aminoalkylboronate ester hydrohalide salt; and (b) neutralizing the β-aminoalkylboronate ester hydrohalide salt to form β- aminoalkylboronate ester.

Included is a process for synthesizing a compound of the formula:

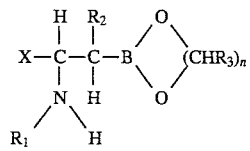

where $R_1$, $R_2$ and $R_3$ are independently hydrogens or $C_1$–$C_4$ alkyls, n is 2–4; and X is aryl, substituted aryl or $C_1$–$C_6$ alkyl.

Preferably a "third step" (c) follows steps (a) and (b) above:

(c) reacting the β-aminoalkylboronic acid with an acylating agent to form β-N-acylaminoboronic acid (most preferred), or with a sulfonating agent to form β-N-sulfonylaminoalkylboronic acid, or with a phosphorylating agent to form β-N-phosphorylaminoalkylboronic acid. This is to introduce the Y functionality. This can also be done for the boronate ester above:

(c) reacting the β-aminoalkylboronate ester with an acylating agent to form β-N-acylaminoboronate ester, or with a sulfonating agent to form β-N-sulfonylaminoalkylboronate ester, or with a β-N-phosphorylating agent to form phosphorylaminoalkylboronate ester.

The sulfonating agent of step (c) for the boronic acid or boronate ester is preferably sulfonyl chloride of the structure:

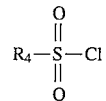

where $R_4$ is $C_1$–$C_4$ alkyl, aryl or substituted aryl.

The acylating agent of step (c) is preferably acid chloride of the structure:

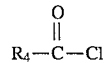

or anhydride of the structure:

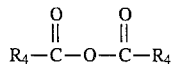

or carboxylic acid of the structure:

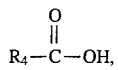

where each $R_4$ is independently $C_1$–$C_4$ alkyl, aryl or substituted aryl

The phosphorylating agent of step (c) preferably has the structure:

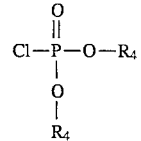

wherein $R_4$ is $C_1$–$C_4$ alkyl, aryl or substituted aryl.

An alternate, preferred "third step" following steps (a) and (b) above is:

(c) reacting the β-aminoalkylboronic acid with an amino acid or a dipeptide or a tripeptide to form a β-N-peptidylaminoalkylboronic acid.

This third step can also be done for the boronate ester:

(c) reacting the β-aminoalkylboronate ester with an amino acid or a dipeptide or a tripeptide to form a β-N-peptidylaminoboronate ester.

The amino acids are preferably selected from the group consisting of alanine, valine, leucine, isoleucine, phenylalanine, glycine, and threonine. Most preferred are glanine, glycine, leucine, valine and phenylalanine.

Dipeptides or tripeptides are preferred over amino acid and preferably comprise amino acids selected from the group consisting of alanine, valine, leucine, isoleucine, phenylalanine, glycine, threonine, and mixtures thereof.

Tripeptides are most preferred and are preferably comprised of amino acids selected from the group consisting of alanine, glycine, leucine, valine, phenylalanine, and mixtures thereof.

Surprisingly, the compounds herein can be prepared in high yield from the requisite trimethylsilylenamine as demonstrated below:

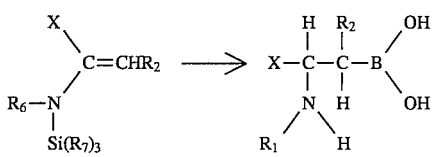

where $R_6$ is $C_1$–$C_4$ alkyl or trialkylsilyl, $R_7$ is independently selected from $C_1$–$C_3$ alkyl, and $R_1$ is defined as above.

Although the trimethylsilylenamines have to be synthesized, there are published routes for their preparation. See for example, Ahlbrecht, H. and Liesching, D., *Synthesis*, pp. 746–748 (1976); Ahlbrecht, H. and Dueber, E., *Synthesis*, pp. 273–275 (1982); and Ahlbrecht, H., and Dueber, E., *Synthesis*, pp. 630–631 (1980), each incorporated herein by reference. β-aminoalkylboronic acids and their peptide, amide, sulfonamide, phosphonamide and urethane derivatives are included herein.

The present invention is preferably a process for synthesizing a β-aminoalkylboronic acid, preferably comprising the steps of:

(a) reacting dibromoborane dimethyl sulfide complex and substituted silylated enamine under positive inert gas pressure to form β-silylaminoalkyldibromoborane;

(b) hydrolyzing the β-silyl aminoalkyldibromoborane to form β-aminoalkylboronic acid hydrobromide salt;

(c) precipitating and collecting the β-aminoalkylboronic acid hydrobromide salt;

(d) dissolving the β-aminoalkylboronic acid hydrobromide salt in water; and after neutralization with sodium hydroxide extracting the β-aminoalkylboronic acid into an organic solvent.

The preferred reaction temperature for step (a) is between room temperature and the boiling point of the solvent, most preferably from about 35° C. to about 45° C. (the boiling point of methylene chloride).

Preferred solvents for the extraction in step (d) above are methylene chloride, diethylether, and chloroform (most preferred).

The preferred substituted silylated enamine in step (a) is:

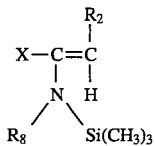

where X is aryl, substituted aryl, or $C_1$–$C_4$ alkyl, and $R_8$ is $Si(CH_3)_3$ or $CH_3$.

The most preferred substituted silylated enamine in step (a) is:

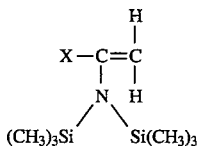

where X is phenyl or isopropyl.

Liquid Detergents Containing the Compound

Included herein are protease-containing liquid detergent compositions containing the compounds described above for the reversible inhibition of serine protease, and stabilization of the protease (i.e. proteolytic enzyme) itself or second enzymes in the composition.

Included is a liquid laundry detergent composition, comprising:

(a) from about 0.001 to 10 weight % of a compound or compounds of the following structure:

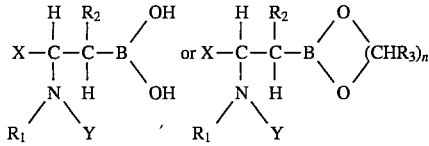

where $R_1$, $R_2$, and $R_3$ are independently hydrogen or $C_1$–$C_4$ alkyl; n is 2–4; X is aryl, substituted aryl or $C_1$–$C_6$ alkyl; Y is selected from the group consisting of hydrogen, amine protecting group, and amino acid, dipeptide or tripeptide linked through the C-terminal carboxylic acid.

(b) from about 0.0001 to 1.0 weight % of active proteolytic enzyme; and (c) from about 1 to 80 weight % of detersive surfactant.

Also included is a liquid detergent composition comprising:

(a) from about 0.001 to 10 weight % of β-aminoalkylboronic acid or β-aminoalkylboronate ester or β-N-peptidylaminoalkylboronic acid or β-N-peptidylaminoalkylboronate ester;

(b) from about 0.0001 to 1.0 weight % of active proteolytic enzyme; and (c) from about 1 to 80 weight % of detersive surfactant.

Proteolytic Enzyme

An essential ingredient in the present liquid detergent composition is from about 0.0001 to 1.0, preferably about 0.0005 to 0.5, most preferably about 0.002 to 0.1, weight % of active proteolytic enzyme. Mixtures of proteolytic enzyme are also included. The proteolytic enzyme can be of animal, vegetable or microorganism (preferred) origin. More preferred is serine proteolytic enzyme of bacterial origin. Purified or nonpurified forms of this enzyme may be used. Proteolytic enzymes produced by chemically or genetically modified mutants are included by definition, as are close structural enzyme variants. Particularly preferred is bacterial serine proteolytic enzyme obtained from *Bacillus subtilis* and/or *Bacillus licheniformis*.

Suitable proteolytic enzymes include Alcalase® (Subtilisin Carlesburg), Esperase®, Savinase® (preferred); Maxatase®, Maxacal® (preferred), and Maxapem 15® (protein engineered Maxacal ®); and subtilisin BPN and BPN' (preferred); which are commercially available. Preferred proteolytic enzymes are also modified bacterial serine proteases, such as those described in European Patent Application Serial Number 87 303761.8, filed Apr. 28, 1987 (particularly pages 17, 24 and 98), and which is called herein "Protease B", and in European Patent Application 199,404, Venegas, published Oct. 29, 1986, which refers to a modified bacterial serine proteolytic enzyme which is called "Protease A" herein. Preferred proteolytic enzymes, then, are selected from the group consisting of Subtilisin Carlesburg, protease derived from *Bacillus licheniformis*, BPN', Protease A and Protease B, and mixtures thereof. Protease B is most preferred.

Second Enzyme

A preferred ingredient in the present liquid compositions is from about 0.0001 to 1.0, preferably 0.001 to 0.5, weight % on an active basis of a detergent-compatible second enzyme. By "detergent-compatible" is meant compatibility with the other ingredients of a liquid detergent composition, such as detersive surfactant and detergency builder. These second enzymes are preferably selected from the group consisting of lipase, amylase, cellulase, and mixtures thereof. The term "second enzyme" excludes the proteolytic enzymes discussed above, so each composition herein contains at least two kinds of enzyme, including at least one proteolytic enzyme.

The amount of second enzyme used in the composition varies according to the type of enzyme and the use intended. In general, from about 0.0001 to 1.0, more preferably 0.001 to 0.5, weight % on an active basis of these second enzymes are preferably used.

Mixtures of enzymes from the same class (e.g. lipase) or two or more classes (e.g. cellulase and lipase) may be used. Purified or non-purified forms of the enzyme may be used.

Any lipase suitable for use in a liquid detergent composition can be used herein. Suitable lipases for use herein include those of bacterial and fungal origin. Second enzymes from chemically or genetically modified mutants are included.

Suitable bacterial lipases include those produced by Pseudomonas, such as *Pseudomonas stutzeri* ATCC 19.154, as disclosed in British Patent 1,372,034, incorporated herein by reference. Suitable lipases include those which show a positive immunological cross-reaction with the antibody of the lipase produced by the microorganism *Pseudomonas fluorescens* IAM 1057. This lipase and a method for its purification have been described in Japanese Patent Application 53-20487, laid open on Feb. 24, 1987, which is incorporated herein by reference. This lipase is available under the trade name Lipase P "Amano," hereinafter referred to as "Amano-P." Such lipases should show a positive immunological cross reaction with the Amano-P antibody, using the standard and well-known immunodiffusion procedure according to Ouchterlony (*Acta. Med. Scan.*, 133, pages 76–79 (1950)). These lipases, and a method for their immunological cross-reaction with Amano-P, are also described in U.S. Pat. No. 4,707,291, Thom et al., issued Nov. 17, 1987, incorporated herein by reference. Typical examples thereof are the Amano-P lipase, the lipase ex *Pseudomonas fragi* FERM P 1339 (available under the trade name Amano-B), lipase ex *Pseudomonas nitroreducens* var. *lipolyticum* FERM P 1338 (available under the trade name Amano-CES), lipases ex *Chromobacter viscosum*, e.g. *Chromobacter viscosum* var. *lipolyticum* NRRLB 3673, and further *Chromobacter viscosum* lipases, and lipases ex *Pseudomonas gladioli*. Other lipases of interest are Amano AKG and Bacillis Sp lipase (e.g., Solvay enzymes).

Other lipases which are of interest where they are detergent-compatible are those described in EP A 0 399 681, published Nov. 28, 1990, EP A 0 385 401, published Sep. 5, 1990, EP A 0 218 272, published Apr. 15, 1987, and PCT/DK 88/00177, published May 18, 1989, all incorporated herein by reference.

Suitable fungal lipases include those producible by *Humicola lanuginosa* and *Thermomyces lanuginosus*. Most preferred is lipase obtained by cloning the gene from *Humicola lanuginosa* and expressing the gene in *Aspergillus oryzae* as described in European Patent Application 0 258 068, incorporated herein by reference, commercially available under the trade name Lipolase®.

From about 2 to 20,000, preferably about 10 to 6,000, lipase units of lipase per gram (LU/g) of product can be used in these compositions. A lipase unit is that amount of lipase which produces 1 μmol of titratable butyric acid per minute in a pH stat, where pH is 7.0, temperature is 30° C., and substrate is an emulsion tributyrin and gum arabic, in the presence of $Ca^{++}$ and NaCl in phosphate buffer.

Any cellulase suitable for use in a liquid detergent composition can be used in these compositions. Suitable cellulase enzymes for use herein include those of bacterial and fungal origins. Preferably, they will have a pH optimum of between 5 and 9.5. From about 0.0001 to 1.0, preferably 0.001 to 0.5, weight % on an active enzyme basis of cellulase can be used.

Suitable cellulases are disclosed in U.S. Pat. No. 4,435,307, Barbesgaard et al., issued Mar. 6, 1984, incorporated herein by reference, which discloses fungal cellulase produced from *Humicola insolens*. Suitable cellulases are also disclosed in GB-A-2.075.028, GB-A-2.095.275 and DE-OS-2.247.832.

Examples of such cellulases are cellulases produced by a strain of *Humicola insolens* (*Humicola grisea* var. *thermoidea*), particularly the Humicola strain DSM 1800, and cellulases produced by a fungus of Bacillus N or a cellulase 212-producing fungus belonging to the genus Aeromonas, and cellulase extracted from the hepatopancreas of a marine mollusc (Dolabella Auricula Solander).

Any amylase suitable for use in a liquid detergent composition can be used in these compositions. Amylases include, for example, α-amylases obtained from a special strain of *B. licheniforms*, described in more detail in British Patent Specification No. 1,296,839. Amylolytic proteins include, for example, Rapidase™, Maxamyl™ and Termamyl™.

From about 0.0001% to 1.0, preferably 0.0005 to 0.5, weight % on an active enzyme basis of amylase can be used.

Detersive Surfactant

From about 1 to 80, preferably about 5 to 50, most preferably about 10 to 30, weight % of detersive surfactant is the fourth essential ingredient in the present invention. The detersive surfactant can be selected from the group consisting of anionics, nonionics, cationics, ampholytics, zwitterionics, and mixtures thereof. Anionic and nonionic surfactants are preferred.

The benefits of the present invention are especially pronounced in compositions containing ingredients that are harsh to enzymes such as certain detergency builders and surfactants. Preferably the anionic surfactant comprises $C_{12}$–$C_{20}$ alkyl sulfate, $C_{12}$ to $_{20}$ alkyl ether sulfate and $C_9$ to $_{20}$ linear alkylbenzene sulfonate. Suitable surfactants are described below.

Heavy duty liquid laundry detergents are the preferred liquid detergent compositions herein. The particular surfactants used can vary widely depending upon the particular end-use envisioned. These compositions will most commonly be used for cleaning of laundry, fabrics, textiles, fibers, and hard surfaces.

Known anionic surfactants are preferred for use herein.

Alkyl sulfate surfactants are a type of anionic surfactant of importance for use herein. Alkyl sulfates have the general formula $ROSO_3M$ wherein R preferably is a $C_{10}$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali metal cation (e.g., sodium, potassium, lithium), substituted or unsubstituted ammonium cations such as methyl-, dimethyl-, and trimethyl ammonium and quaternary ammonium cations, e.g., tetramethyl-ammonium and dimethyl piperdinium, and cations derived from alkanolamines such as ethanolamine, diethanolamine, triethanolamine, and mixtures thereof, and the like. Typically, alkyl chains of $C_{12-16}$ are preferred for lower wash temperatures (e.g., below about 50° C.) and $C_{16-18}$ alkyl chains are preferred for higher wash temperatures (e.g., above about 50° C.).

Alkyl alkoxylated sulfate surfactants are another category of useful anionic surfactant. These surfactants are water soluble salts or acids typically of the formula $RO(A)_mSO_3M$ wherein R is an unsubstituted $C_{10}$–$C_{24}$ alkyl or hydroxyalkyl group having a $C_{10}$–$C_{24}$ alkyl component, preferably a $C_{12}$–$C_{20}$ alkyl or hydroxyalkyl, more preferably $C_{12}$–$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl-, trimethyl-ammonium and quaternary ammonium cations, such as tetramethyl-ammonium, dimethyl piperydinium and cations derived from alkanolamines, e.g. monoethanolamine, diethanolamine, and triethanolamine, and mixtures thereof. Exemplary surfactants are $C_{12}$–$C_{18}$ alkyl polyethoxylate (1.0) sulfate, $C_{12}$–$C_{18}$ alkyl polyethoxylate (2.25) sulfate, $C_{12}$–$C_{18}$ alkyl polyethoxylate (3.0) sulfate, and $C_{12}$–$C_{18}$ alkyl polyethoxylate (4.0) sulfate wherein M is conveniently selected from sodium and potassium.

Other anionic surfactants useful for detersive purposes can also be included in the compositions hereof. These can include salts (including, for example, sodium, potassium, ammonium, and substituted ammonium salts such as mono-, di- and triethanolamine salts) of soap, $C_9$–$C_{20}$ linear alkylbenzenesulphonates, $C_8$–$C_{22}$ primary or secondary alkanesulphonates, $C_8$–$C_{24}$ olefinsulphonates, sulphonated polycarboxylic acids, alkyl glycerol sulfonates, fatty acyl glycerol sulfonates, fatty oleyl glycerol sulfates, alkyl phenol ethylene oxide ether sulfates, paraffin sulfonates, alkyl phosphates, isothionates such as the acyl isothionates, N-acyl taurates, fatty acid amides of methyl tauride, alkyl succinamates and sulfosuccinates, monoesters of sulfosuccinate (especially saturated and unsaturated $C_{12}$–$C_{18}$ monoesters) diesters of sulfosuccinate (especially saturated and unsaturated $C_6$–$C_{14}$ diesters), N-acyl sarcosinates, sulfates of alkylpolysaccharides such as the sulfates of alkylpolyglucoside, branched primary alkyl sulfates, alkyl polyethoxy carboxylates such as those of the formula $RO(CH_2CH_2O)_kCH_2COO^-M^+$ wherein R is a $C_8$–$C_{22}$ alkyl, k is an integer from 0 to 10, and M is a soluble salt-forming cation, and fatty acids esterified with isethionic acid and neutralized with sodium hydroxide. Further examples are given in *Surface Active Agents and Detergents* (Vol. I and II by Schwartz, Perry and Berch). *Nonionic Detergent Surfactants*

Suitable nonionic detergent surfactants are generally disclosed in U.S. Pat. No. 3,929,678, Laughlin et al., issued Dec. 30, 1975, at column 13, line 14 through column 15, line 6, incorporated herein by reference. Exemplary, non-limiting classes of useful nonionic surfactants are listed below.

1. The polyethylene, polypropylene, and polybutylene oxide condensates of alkyl phenols. In general, the polyethylene oxide condensates are preferred. These compounds include the condensation products of alkyl phenols having an alkyl group containing from about 6 to about 12 carbon atoms in either a straight chain or branched chain configuration with the alkylene oxide. These compounds are commonly referred to as alkyl phenol alkoxylates, (e.g., alkyl phenol ethoxylates).

2. The condensation products of aliphatic alcohols with from about 1 to about 25 moles of ethylene oxide. The alkyl chain of the aliphatic alcohol can either be straight or branched, primary or secondary, and generally contains from about 8 to about 22 carbon atoms. Particularly preferred are the condensation products of alcohols having an alkyl group containing from about 10 to about 20 carbon atoms with from about 2 to about 18 moles of ethylene oxide per mole of alcohol.

3. The condensation products of ethylene oxide with a hydrophobic base formed by the condensation of propylene oxide with propylene glycol. Examples of compounds of this type include certain of the commercially-available Pluronic™ surfactants, marketed by BASF.

4. The condensation products of ethylene oxide with the product resulting from the reaction of propylene oxide and ethylenediamine. Examples of this type of nonionic surfactant include certain of the commercially available Tetronic™ compounds, marketed by BASF.

5. Semi-polar nonionic surfactants are a special category of nonionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety of from about 10 to about 18 carbon atoms 31 and a moiety selected from the group consisting of alkyl and hydroxyalkyl moieties of from about 1 to about 3 carbon atoms.

Semi-polar nonionic detergent surfactants include the amine oxide surfactants having the formula:

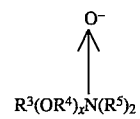

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3; and each $R^5$ is an alkyl or hydroxyalkyl group containing from about 1 to about 3 carbon atoms or a polyethylene oxide group containing from about 1 to about 3 ethylene oxide groups. The $R^5$ groups can be attached to each other, e.g., through an oxygen or nitrogen atom, to form a ring structure.

These amine oxide surfactants in particular include $C_{10}$–$C_{18}$ alkyl dimethyl amine oxides and $C_8$–$C_{12}$ alkoxy ethyl dihydroxy ethyl amine oxides.

6. Alkylpolysaccharides disclosed in U.S. Pat. No. 4,565, 647, Llenado, issued Jan. 21, 1986, having a hydrophobic group containing from about 6 to about 30 carbon atoms, preferably from about 10 to about 16 carbon atoms and a polysaccharide, e.g., a polyglycoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties. (Optionally the hydrophobic group is attached at the 2-, 3-, 4-, etc. positions thus giving a glucose or galactose as opposed to a glucoside or galactoside.) The intersaccharide bonds can be, e.g., between the one position of the additional saccharide units and the 2-, 3-, 4-, and/or 6-positions on the preceding saccharide units.

7. Fatty acid amide surfactants having the formula:

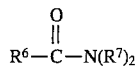

wherein $R^6$ is an alkyl group containing from about 7 to about 21 (preferably from about 9 to about 17) carbon atoms and each $R^7$ is selected from the group consisting of hydrogen, $C_1$–$C_4$ alkyl, $C_1$–$C_4$ hydroxyalkyl, and —$(C_2H_4O)_xH$ where x varies from about 1 to about 3.

Preferred amides are $C_8$–$C_{20}$ ammonia amides, monoethanolamides, diethanolamides, and isopropanolamides.

Polyhydroxy Fatty Acid Amide Surfactant

The detergent compositions may preferably comprise from about 3 to 50 weight %, most preferably from about 3% to 30%, of the polyhydroxy fatty acid amide.

The polyhydroxy fatty acid amide surfactant component comprises compounds of the structural formula:

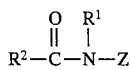

wherein: $R^1$ is H, $C_1$–$C_4$ hydrocarbyl, 2-hydroxy ethyl, 2-hydroxy propyl, or a mixture thereof, preferably $C_1$–$C_4$ alkyl, more preferably $C_1$ or $C_2$ alkyl, most preferably $C_1$ alkyl (i.e., methyl); and $R^2$ is a $C_5$–$C_{31}$ hydrocarbyl, preferably straight chain $C_7$–$C_{19}$ alkyl or alkenyl, more preferably straight chain $C_9$–$C_{17}$ alkyl or alkenyl, most preferably straight chain $C_{11}$–$C_{15}$ alkyl or alkenyl, or mixtures thereof; and Z is a polyhydroxyhydrocarbyl having a linear hydrocarbyl chain with at least 3 hydroxyls directly connected to the chain, or an alkoxylated derivative (preferably ethoxylated or propoxylated) thereof. Z preferably will be derived from a reducing sugar in a reductive amination reaction; more preferably Z will be a glycityl. Suitable reducing sugars include glucose, fructose, maltose, lactose, galactose, mannose, and xylose. As raw materials, high dextrose corn syrup, high fructose corn syrup, and high maltose corn syrup can be utilized as well as the individual sugars listed above. These corn syrups may yield a mix of sugar components for Z. It should be understood that it is by no means intended to exclude other suitable raw materials. Z preferably will be selected from the group consisting of —$CH_2$—$(CHOH)_n$—$CH_2OH$, —$CH(CH_2OH)$—$(CHOH)_{n-1}$—$CH_2OH$, —$CH_2$—$(CHOH)_2(CHOR')$ $(CHOH)$—$CH_2OH$, and alkoxylated derivatives thereof, where n is an integer from 3 to 5, inclusive, and R' is H or a cyclic or aliphatic monosaccharide. Most preferred are glycityls wherein n is 4, particularly —$CH_2$—$(CHOH)_4$—$CH_2OH$.

In Formula (I), R' can be, for example, N-methyl, N-ethyl, N-propyl, N-isopropyl, N-butyl, N-2-hydroxy ethyl, or N-2-hydroxy propyl.

$R^2$—CO—N< can be, for example, cocamide, stearamide, oleamide, lauramide, myristamide, capricamide, palmitamide, tallowamide, etc.

Z can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

Other Surfactants

Ampholytic surfactants can be incorporated into the detergent compositions hereof. These surfactants can be broadly described as aliphatic derivatives of secondary or tertiary amines, or aliphatic derivatives of heterocyclic secondary and tertiary amines in which the aliphatic radical can be straight chain or branched. One of the aliphatic substituents contains at least about 8 carbon atoms, typically from about 8 to about 18 carbon atoms, and at least one contains an anionic water-solubilizing group, e.g., carboxy, sulfonate, sulfate. See U.S. Pat. No. 3,929,678 to Laughlin et al., issued Dec. 30, 1975 at column 19, lines 18–35 (herein incorporated by reference) for examples of ampholytic surfactants.

Zwitterionic surfactants can also be incorporated into the detergent compositions hereof. These surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 to Laughlin et al., issued Dec. 30, 1975 at column 19, line 38 through column 22, line 48 (herein incorporated by reference) for examples of zwitterionic surfactants.

Ampholytic and zwitterionic surfactants are generally used in combination with one or more anionic and/or nonionic surfactants.

Optional Ingredients

Detergency Builders

From 0 to about 50, preferably about 3 to 30, more preferably about 5 to 20, weight % detergency builder can be included herein. Inorganic as well as organic builders can be used.

Inorganic detergency builders include, but are not limited to, the alkali metal, ammonium and alkanolammonium salts of polyphosphates (exemplified by the tripolyphosphates, pyrophosphates, and glassy polymeric meta-phosphates), phosphonates, phytic acid, silicates, carbonates (including bicarbonates and sesquicarbonates), sulphates, and aluminosilicates. Borate builders, as well as builders containing borate-forming materials that can produce borate under detergent storage or wash conditions (hereinafter, collectively "borate builders"), can also be used. Preferably, non-borate builders are used in the compositions of the invention intended for use at wash conditions less than about 50° C., especially less than about 40° C.

Examples of silicate builders are the alkali metal silicates, particularly those having a $SiO_2$:$Na_2O$ ratio in the range 1.6:1 to 3.2:1 and layered silicates, such as the layered sodium silicates described in U.S. Pat. No. 4,664,839, issued May 12, 1987 to H. P. Rieck, incorporated herein by reference. However, other silicates may also be useful such as for example magnesium silicate, which can serve as a crispening agent in granular formulations, as a stabilizing agent for oxygen bleaches, and as a component of suds control systems.

Examples of carbonate builders are the alkaline earth and alkali metal carbonates, including sodium carbonate and sesquicarbonate and mixtures thereof with ultra-fine calcium carbonate as disclosed in German Patent Application No. 2,321,001 published on Nov. 15, 1973, the disclosure of which is incorporated herein by reference.

Aluminosilicate builders are useful in the present invention. Aluminosilicate builders are of great importance in most currently marketed heavy duty granular detergent compositions, and can also be a significant builder ingredient in liquid detergent formulations. Aluminosilicate builders include those having the empirical formula:

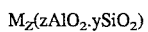

wherein M is sodium, potassium, ammonium or substituted ammonium, z is from about 0.5 to about 2; and y is 1; this material having a magnesium ion exchange capacity of at least about 50 milligram equivalents of $CaCO_3$ hardness per gram of anhydrous aluminosilicate. Preferred aluminosilicates are zeolite builders which have the formula:

$$Na_z[(AlO_2)_z(SiO_2)_y]\cdot xH_2O$$

wherein z and y are integers of at least 6, the molar ratio of z to y is in the range from 1.0 to about 0.5, and x is an integer from about 15 to about 264.

Specific examples of polyphosphates are the alkali metal tripolyphosphates, sodium, potassium and ammonium pyrophosphate, sodium and potassium and ammonium pyrophosphate, sodium and potassium orthophosphate, sodium polymeta phosphate in which the degree of polymerization ranges from about 6 to about 21, and salts of phytic acid.

Organic detergent builders preferred for the purposes of the present invention include a wide variety of polycarboxylate compounds. As used herein, "polycarboxylate" refers to compounds having a plurality of carboxylate groups, preferably at least 3 carboxylates.

Polycarboxylate builder can generally be added to the composition in acid form, but can also be added in the form of a neutralized salt. When utilized in salt form, alkali metals, such as sodium, potassium, and lithium, or alkanolammonium salts are preferred.

Included among the polycarboxylate builders are a variety of categories of useful materials. One important category of polycarboxylate builders encompasses the ether polycarboxylates. A number of ether polycarboxylates have been disclosed for use as detergent builders. Examples of useful ether polycarboxylates include oxydisuccinate, as disclosed in Berg, U.S. Pat. No. 3,128,287, issued Apr. 7, 1964, and Lamberti et al. U.S. Pat. No. 3,635,830, issued Jan. 18, 1972, both of which are incorporated herein by reference.

A specific type of ether polycarboxylates useful as builders in the present invention also include those having the general formula:

$$CH(A)(COOX)—CH(COOX)—O—CH(COOX)—CH(COOX)(B)$$

wherein A is H or OH; B is H or $—O—CH(COOX)—CH_2(COOX)$; and X is H or a salt-forming cation. For example, if in the above general formula A and B are both H, then the compound is oxydissuccinic acid and its water-soluble salts. If A is OH and B is H, then the compound is tartrate monosuccinic acid (TMS) and its water-soluble salts. If A is H and B is $—O—CH(COOX)—CH_2(COOX)$, then the compound is tartrate disuccinic acid (TDS) and its water-soluble salts. Mixtures of these builders are especially preferred for use herein. Particularly preferred are mixtures of TMS and TDS in a weight ratio of TMS to TDS of from about 97:3 to about 20:80. These builders are disclosed in U.S. Pat. No. 4,663,071, issued to Bush et al., on May 5, 1987.

Suitable ether polycarboxylates also include cyclic compounds, particularly alicyclic compounds, such as those described in U.S. Pat. Nos. 3,923,679; 3,835,163; 4,158,635; 4,120,874 and 4,102,903, all of which are incorporated herein by reference.

Other useful detergency builders include the ether hydroxypolycarboxylates represented by the structure:

$$HO—[C(R)(COOM)—C(R)(COOM)—O]_n—H$$

wherein M is hydrogen or a cation wherein the resultant salt is water-soluble, preferably an alkali metal, ammonium or substituted ammonium cation, n is from about 2 to about 15 (preferably n is from about 2 to about 10, more preferably n averages from about 2 to about 4) and each R is the same or different and selected from hydrogen, $C_{1-4}$ alkyl or $C_{1-4}$ substituted alkyl (preferably R is hydrogen).

Still other ether polycarboxylates include copolymers of maleic anhydride with ethylene or vinyl methyl ether, 1, 3, 5-trihydroxy benzene-2, 4, 6-trisulphonic acid, and carboxymethyloxysuccinic acid.

Organic polycarboxylate builders also include the various alkali metal, ammonium and substituted ammonium salts of polyacetic acids. Examples include the sodium, potassium, lithium, ammonium and substituted ammonium salts of ethylenediamine tetraacetic acid, and nitrilotriacetic acid.

Also included are polycarboxylates such as mellitic acid, succinic acid, oxydisuccinic acid, polymaleic acid, benzene 1,3,5-tricarboxylic acid, and carboxymethyloxysuccinic acid, and soluble salts thereof.

Citrate builders, e.g., citric acid and soluble salts thereof (particularly sodium salt), are polycarboxylate builders of particular importance for heavy duty liquid detergent formulations, but can also be used in granular compositions.

Other carboxylate builders include the carboxylated carbohydrates disclosed in U.S. Pat. No. 3,723,322, Diehl, issued Mar. 28, 1973, incorporated herein by reference.

Also suitable in the detergent compositions of the present invention are the 3,3-dicarboxy-4-oxa-1,6-hexanedioates and the related compounds disclosed in U.S. Pat. No. 4,566,984, Bush, issued Jan. 28, 1986, incorporated herein by reference. Useful succinic acid builders include the $C_5$–$C_{20}$ alkyl succinic acids and salts thereof. A particularly preferred compound of this type is dodecenylsuccinic acid. Alkyl succinic acids typically are of the general formula $R—CH(COOH)CH_2(COOH)$ i.e., derivatives of succinic acid, wherein R is hydrocarbon, e.g., $C_{10}$–$C_{20}$ alkyl or alkenyl, preferably $C_{12}$–$C_{16}$ or wherein R may be substituted with hydroxyl, sulfo, sulfoxy or sulfone substituents, all as described in the above-mentioned patents.

The succinate builders are preferably used in the form of their water-soluble salts, including the sodium, potassium, ammonium and alkanolammonium salts.

Specific examples of succinate builders include: laurylsuccinate, myristylsuccinate, palmitylsuccinate, 2-dodecenylsuccinate (preferred), 2-pentadecenylsuccinate, and the like. Laurylsuccinates are the preferred builders of this group, and are described in European Patent Application 86200690.5/0,200,263, published Nov. 5, 1986.

Examples of useful builders also include sodium and potassium carboxymethyloxymalonate, carboxymethyloxysuccinate, cis-cyclohexane-hexacarboxylate, cis-cyclopentane-tetracarboxylate, water-soluble polyacrylates (these polyacrylates having molecular weights to above about 2,000 can also be effectively utilized as dispersants), and the copolymers of maleic anhydride with vinyl methyl ether or ethylene.

Other suitable polycarboxylates are the polyacetal carboxylates disclosed in U.S. Pat. No. 4,144,226, Crutchfield et al., issued Mar. 13, 1979, incorporated herein by reference. These polyacetal carboxylates can be prepared by bringing together, under polymerization conditions, an ester of glyoxylic acid and a polymerization initiator. The resulting polyacetal carboxylate ester is then attached to chemically stable end groups to stabilize the polyacetal carboxylate against rapid depolymerization in alkaline solution, converted to the corresponding salt, and added to a surfactant.

Polycarboxylate builders are also disclosed in U.S. Pat. No. 3,308,067, Diehl, issued Mar. 7, 1967, incorporated herein by reference. Such materials include the water-soluble salts of homo- and copolymers of aliphatic carboxylic acids such as maleic acid, itaconic acid, mesaconic acid, fumaric acid, aconitic acid, citraconic acid and methylenemalonic acid.

Other organic builders known in the art can also be used. For example, monocarboxylic acids, and soluble salts thereof, having long chain hydrocarbyls can be utilized. These would include materials generally referred to as "soaps." Chain lengths of $C_{10}$–$C_{20}$ are typically utilized. The hydrocarbyls can be saturated or unsaturated.

Soil Release Agent

Any soil release agents known to those skilled in the art can be employed in the practice of this invention.

Useful soil release polymers are described in U.S. Pat. No. 4,000,093, issued Dec. 28, 1976 to Nicol et al., European Patent Application 0 219 048, published Apr. 22, 1987 by Kud et al. U.S. Pat. No. 3,959,230 to Hays, issued May 25, 1976, U.S. Pat. No. 3,893,929 to Basadur issued Jul. 8, 1975, U.S. Pat. No. 4,702,857, issued Oct. 27, 1987 to Gosselink, U.S. Pat. No. 4,711,730, issued Dec. 8, 1987 to Gosselink et al., U.S. Pat. No. 4,721,580, issued Jan. 26, 1988 to Gosselink, U.S. Pat. No. 4,702,857, issued Oct. 27, 1987 to Gosselink, U.S. Pat. No. 4,877,896, issued Oct. 31, 1989 to Maldonado et al. All of these patents are incorporated herein by reference.

If utilized, soil release agents will generally comprise from about 0.01% to about 10.0%, by weight, of the detergent compositions herein, typically from about 0.1% to about 5%, preferably from about 0.2% to about 3.0%.

Clay Soil Removal/Anti-redeposition Agents

The compositions of the present invention can also optionally contain water-soluble ethoxylated amines having clay soil removal and anti-redeposition properties. Liquid detergent compositions which contain these compounds typically contain from about 0.01% to 5%.

The most preferred soil release and anti-redeposition agent is ethoxylated tetraethylenepentamine. Exemplary ethoxylated amines are further described in U.S. Pat. No. 4,597,898, VanderMeer, issued Jul. 1, 1986, incorporated herein by reference. Another group of preferred clay soil removal/anti-redeposition agents are the cationic compounds disclosed in European Patent Application 111,965, Oh and Gosselink, published Jun. 27, 1984, incorporated herein by reference. Other clay soil removal/anti-redeposition agents which can be used include the ethoxylated amine polymers disclosed in European Patent Application 111,984, Gosselink, published Jun. 27, 1984; the zwitterionic polymers disclosed in European Patent Application 112,592, Gosselink, published Jul. 4, 1984; and the amine oxides disclosed in U.S. Pat. No. 4,548,744, Connor, issued Oct. 22, 1985, all of which are incorporated herein by reference.

Other clay soil removal and/or anti redeposition agents known in the art can also be utilized in the compositions hereof. Another type of preferred anti-redeposition agent includes the carboxymethylcellulose (CMC) materials. These materials are well known in the art.

Polymeric Dispersing Agents

Polymeric dispersing agents can advantageously be utilized in the compositions hereof. These materials can aid in calcium and magnesium hardness control. Suitable polymeric dispersing agents include polymeric polycarboxylates and polyethylene glycols, although others known in the art can also be used.

Suitable polymeric dispersing agents for use herein are described in U.S. Pat. No. 3,308,067, Diehl, issued Mar. 7, 1967, and European Patent Application No. 66915, published Dec. 15, 1982, both incorporated herein by reference.

Brightener

Any suitable optical brighteners or other brightening or whitening agents known in the art can be incorporated into the detergent compositions hereof.

Commercial optical brighteners which may be useful in the present invention can be classified into subgroups which include, but are not necessarily limited to, derivatives of stilbene, pyrazoline, coumarin, carboxylic acid, methinecyanines, dibenzothiphene-5,5-dioxide, azoles, 5- and 6-membered-ring heterocycles, and other miscellaneous agents. Examples of such brighteners are disclosed in *The Production and Application of Fluorescent Brightening Agents*, M. Zahradnik, published by John Wiley & Sons, New York (1982), the disclosure of which is incorporated herein by reference.

Subs Suppressors

Compounds known, or which become known, for reducing or suppressing the formation of suds can be incorporated into the compositions of the present invention. Suitable suds suppressors are described in Kirk Othmer Encyclopedia of Chemical Technology, Third Edition, Volume 7, pages 430–447 (John Wiley & Sons, Inc., 1979), U.S. Pat. No. 2,954,347, issued Sep. 27, 1960 to St. John, U.S. Pat. No. 4,265,779, issued May 5, 1981 to Gandolfo et al., U.S. Pat. No. 4,265,779, issued May 5, 1981 to Gandolfo et al. and European Patent Application No. 89307851.9, published Feb. 7, 1990, U.S. Pat. No. 3,455,839, German Patent Application DOS 2,124,526, U.S. Pat. No. 3,933,672, Bartolotta et al., and U.S. Pat. No. 4,652,392, Baginski et al., issued Mar. 24, 1987. All are incorporated herein by reference.

The compositions hereof will generally comprise from 0% to about 5% of suds suppressor.

Other Ingredients

A wide variety of other ingredients useful in detergent compositions can be included in the compositions hereof, including other active ingredients, carriers, hydrotropes, processing aids, dyes or pigments, solvents for liquid formulations, bleaches, bleach activators, etc.

Liquid detergent compositions can contain water and other solvents as carriers. Low molecular weight primary or secondary alcohols exemplified by methanol, ethanol, propanol, and isopropanol are suitable. Monohydric alcohols are preferred for solubilizing surfactant, but polyols such as those containing from 2 to about 6 carbon atoms and from 2 to about 6 hydroxy groups (e.g., propylene glycol, ethylene glycol, glycerine, and 1,2-propanediol) can also be used.

Ethylenediamine-N,N'-disuccinic Acid

The liquid laundry detergent compositions hereof preferably comprise, as the detergency builder, from about 10% to about 18% by weight of a $C_{10}$–$C_{18}$ alkyl monocarboxylic acid, and from about 0.2% to about 10% by weight of citric acid or a salt thereof.

These are described in U.S. Pat. No. 4,704,233, Hartman et al, issued Nov. 3, 1987, which is incorporated herein by reference. The compositions preferably comprise from about 1.5% to about 5% ethylenediamine-N-N'-disuccinic acid or alkali metal, alkaline earth, ammonium or substituted ammonium salts thereof, or mixture thereof. The ethylenediamine-N,N'-disuccinic acid compounent is selected from the group consisting of ethylenediamine-N,N'-disuccinic acid free acid; ethylenediamine-N,N'-disuccinic acid potassium salt; ethylenediamine-N,N'-disuccinic acid ammonium salt; and mixtures thereof.

Liquid Compositions

Preferred heavy duty liquid laundry detergent compositions hereof will preferably be formulated such that during use in aqueous cleaning operations, the wash water will have a pH of between about 6.5 and 11.0, preferably between about 7.0 and 8.5.

The compositions herein preferably have a pH in a 10% solution in water at 20° C. of between about 6.5 to 11.0, preferably 7.0 to 8.5. Techniques for controlling pH at recommended usage levels include the use of buffers, alkalis, acids, etc., and are well known to those skilled in the art.

This invention further provides a method for cleaning substrate, such as fibers, fabrics, hard surfaces, skin, etc., by contacting the substrate, with a liquid detergent composition comprising detersive surfactant, proteolytic enzyme, a detergent-compatible second enzyme (optional), and the compounds described above. Agitation is preferably provided for enhancing cleaning. Suitable means for providing agitation include rubbing by hand or preferably with use of a brush, sponge, cloth, mop, or other cleaning device, automatic laundry washing machines, automatic dishwashers, etc.

Preferred herein are concentrated liquid detergent compositions. By "concentrated" is meant that these compositions will deliver to the wash the same amount of active detersive ingredients at a reduced dosage. Typical regular dosage of heavy duty liquids is 118 milliliters in the U.S. (about ½ cup) and 180 milliliters in Europe.

Concentrated heavy duty liquids herein contain about 10 to 100 weight % more active detersive ingredients than regular heavy duty liquids, and are dosed at less than ½ cup depending upon their active levels. This invention becomes even more useful in concentrated formulations because there are more actives to interfere with enzyme performance. Preferred are heavy duty liquid laundry detergent compositions with from about 30 to 90, preferably 40 to 80, most preferably 50 to 60, weight % of active detersive ingredients.

The following examples illustrate the compositions of the present invention. All parts, percentages and ratios used herein are by weight unless otherwise specified.

EXAMPLE I

Preparation of 2-N-acetylamino-2-phenylethaneboronic acid, compound (4) via hydroboration of an enamine.

The synthesis is conducted according to the following scheme.

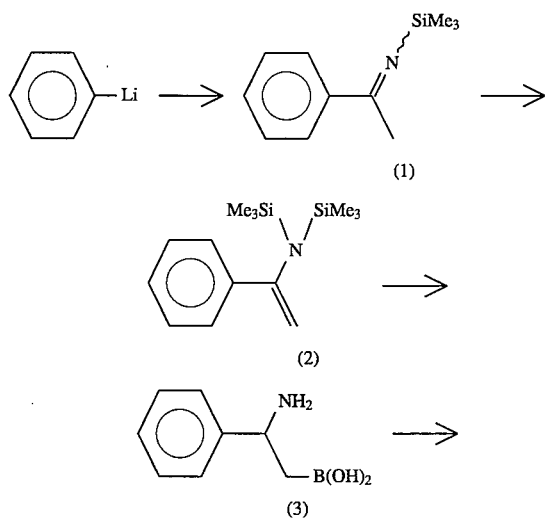

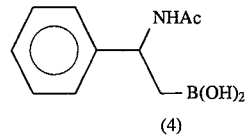

To a 500 ml, three necked, round bottom flask equipped with gas inlet, septa, and thermometer is added acetonitrile (500 g, 122 mmoles) and ether (100 ml). After chilling this solution to 0° C. (ice bath) under a positive argon atmosphere, phenyl lithium (64 ml, 1.6M in benzene-ether, 102 mmoles) is added slowly via syringe over the course of 45 minutes. After complete addition of the phenyl lithium, trimethylchlorosilane(11.08 g, 102 mmoles) is also added via syringe and the reaction is allowed to stir at 0° C. for two additional hours. The ether is then removed under reduced pressure and the product compound (1) isolated by fractional distillation.

Into a 250 ml, three necked round bottom flask fitted with an overhead stirrer, septa and gas inlet is added triethylamine (10.77 g, 106 mmoles), compound (1) (10.02 g, 53.2 moles), and benzene (100 ml). While stirring this solution at room temperature under positive argon pressure, trimethylsilyltriflate (12.83 g, 58.5 mmoles) is added. Stirring is continued for 100 minutes before transferring the bottom layer of the two phase mixture by cannula to a round bottom flask. Compound (2) is isolated by fractional distillation.

Compound (2) (6.01 g, 23.3 mmoles) is immediately transferred via syringe to a 250 ml three neck round bottom flask fitted with thermometer, septa, and condenser/gas inlet. While under positive argon pressure methylene chloride (50 ml) is added followed by dibromoborane dimethyl sulfide (24 ml, 1.0M in methylene chloride, 24 mmoles). The reaction is stirred at reflux (40° C. oil bath) (~16 hrs). After cooling to room temperature, water (1.05 g) is added slowly with accompanying gas evolution and the reaction is stirred for two hours. During this period the amine hydrobromide forms as a precipitate which is collected by filtration. The amine hydrobromide salt (3.04 g, 11.7 mmoles) is dissolved in water and titrated to a pH of 7. The free amine 3 is extracted into chloroform and isolated after removal of the solvent under reduced pressure.

The amine is dissolved in dioxane (50 ml) in a round bottom flask equipped with a condenser. While under argon, acetic anhydride (25 ml) is added and the solution brought to reflux for 1 hour. After the reaction is cooled to room temperature, the solvents are removed under reduced pressure and the product is recrystallized from water to afford leaf-like crystals of compound (4).

EXAMPLE II

Preparation of 2-N-acetylamino-3-methylbutaneboronic acid, compound (7).

The synthesis is conducted according to the following scheme.

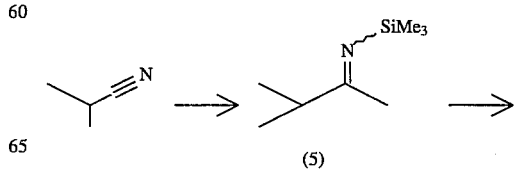

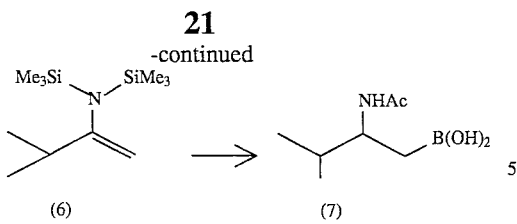

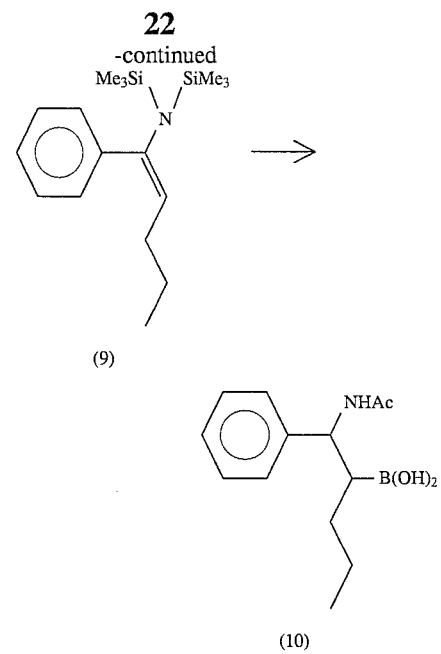

To a solution of isobutyronitrile (1.73 g, 25 mmoles) in THF (30 ml) cooled to −10° C. under an argon atmosphere is slowly added a solution of methyl lithium (15 ml, 1.4M in ether, 21 mmoles). Once the addition is complete the reactions is stirred at 0° C. for 1 hour. Trimethylchlorosilane (2.28 g, 21 mmoles) is then added dropwise to the reaction at 0° C. and after stirring an additional two hours at room temperature, the reaction is distilled to yield 5. To a solution of compound (5) (3.0 g, 19.1 mmoles) in THF (15 ml), which is cooled to −78° C. under an argon atmosphere, is added lithium diisopropylamide (13 ml, 1.5M in THF/heptane, 19.5 mmoles). The reaction is stirred at −78° C. for two hours and quenched by the addition of chlorotrimethylsilane (2.17 g, 20 mmoles). After the addition, the reaction is allowed to warm to room temperature where it is fractionally distilled to afford compound (6).

Compound (6) (2.0 g., 8.7 mmoles) in methylene chloride (25 ml) is mixed with dibromoborane dimethyl sulfide comples (9.0 ml, 1.0M in methylene chloride, 9.0 mmoles) and the solution is refluxed under argon for 16 hours. After cooling to room temperature, water (0.4 ml) is added slowly and the reaction is stirred at room temperature for an additional 2 hours. The solution is neutralized with basic ion exchange resin and the solvent removed under reduced pressure. The residue is taken up in acetic anhydride (10 ml) and refluxed for 1 hour. The solvents are removed under reduced pressure to afford compound (7).

EXAMPLE III

Preparation of 2-N-acetylamino-2-phenyl-1-propylethaneboronic acid, compound (10).

The synethsis is conducted according to the following scheme.

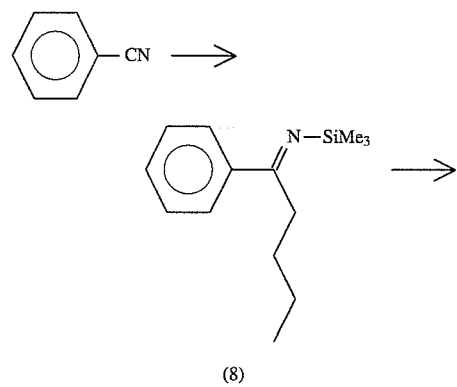

The procedure for the preparation of compounds (8), (9) and (10) is nearly identical to that described in Example I. Benzonitrile is substituted for acetonitrile and n-butyllithum for phenyllithum.

EXAMPLE IV

Preparation of 2-N-[Ala-CBZ]amino-2-phenylethaneboronic acid, compound (12). (CBZ-Ala-βPhe-Bor).

The synthesis is conducted according to the following scheme.

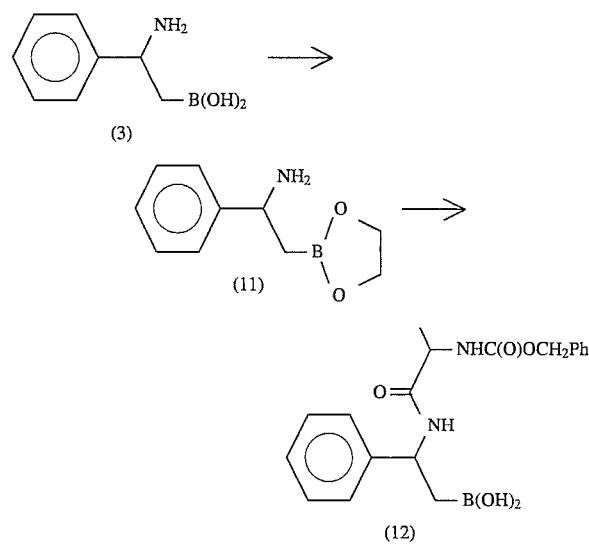

Compound (3) is prepared by the procedure described in Example I. Compound (11) is synthesized by preparing a solution of (3) (2.06 g, 12.5 mmoles) in dichloromethane (30 ml) and adding ethylene glycol (0.85 g, 13.7 mmoles). The reaction is shaken for 20 minutes at room temperature and then stirred over solid $Na_2SO_4$. Removal of the volatiles under reduced pressure affords compound (11). Compound (12) is prepared by the sequential addition of compound (11) (1.5 g, 7.85 mmoles) dissolved in dichloromethane (5 ml), CBZ-Ala (1.75 g, 7.88 mmoles) dissolved in dichloromethane (5 ml), and triethylamine (1.75 g, 17 mmoles)

also dissolved in dichloromethane (5 ml) to a 100 round bottom flask containing dichloromethane (50 ml), and fitted with a gas inlet and a septum. While constantly stirring this solution at room temperature under an inert atmosphere, diethyl cyanophosphonate (1.41 g, 8.64 mmoles) is added slowly. The reaction is stirred overnight. After removing the volatiles under reduced pressure, the residue is dissolved in ethyl acetate (50 ml) and extracted with one portion (20 ml) of 2N HCl in a separatory funnel. The funnel is shaken for 12 minutes until compound (12) precipitates and is suspended in the aqueous layer. Compound (12) is collected by filtration and dried under vacuum.

EXAMPLE V

Preparation of 2-N-[Ala-Gly-CBZ]amino-2-phenylethaneboronic acid, compound (13). (CBZ-Gly-Ala-βPhe-Bor).

The synthesis is conducted according to the following scheme.

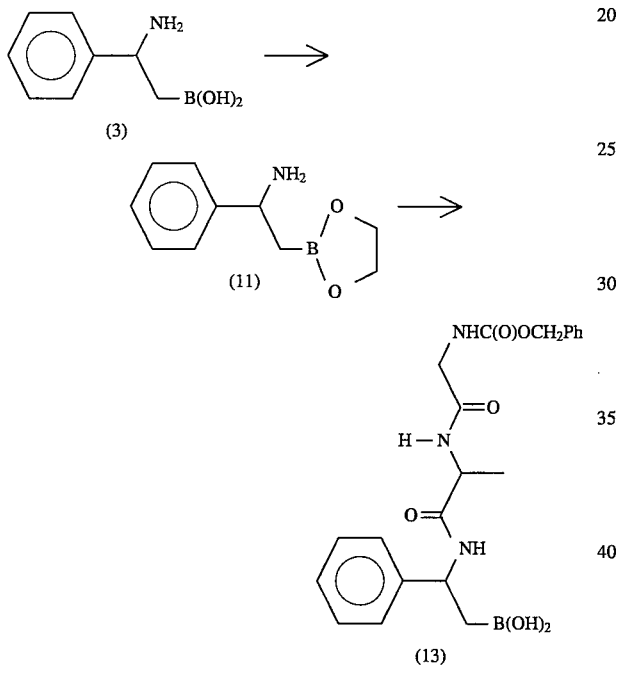

Compound (11) is prepared by the procedure described in Example V. Compound (13) is prepared by the sequential addition of compound (11) (1.0 g, 5.2 mmoles) dissolved in dichloromethane (5 ml), CBZ-Gly-Ala (1.70 g, 6.1 mmoles) dissolved in dichloromethane (5 ml), and triethylamine (1.35 g, 13.3 mmoles), which is also dissolved in dichloromethane (5 ml), to a 100 ml round bottom flask containing dichloromethane (30 ml), and fitted with a gas inlet and a septum. While constantly stirring this solution at room temperature under an inert atmosphere, diethylcyanophosphonate (1.09 g, 6.7 mmoles) is added slowly. The reaction is stirred overnight. After removing the volatiles under reduced pressure, the residue is dissolved in ethyl acetate (30 ml) and extracted with one portion (15 ml) of 2N HCl in a separatory funnel. The funnel is shaken for 12 minutes until compound (13) precipitates and is suspended in the aqueous layer. Compound (13 is collected by filtration and dried under vacuum.

EXAMPLE VI

Preparation of 2-N-[Phe-Ala-Gly-MOC]amino-2-phenylethaneboronic acid, compound (18). (MOC-Phe-Gly-Ala-BPhe-Bor).

The synthesis is conducted according to the following scheme.

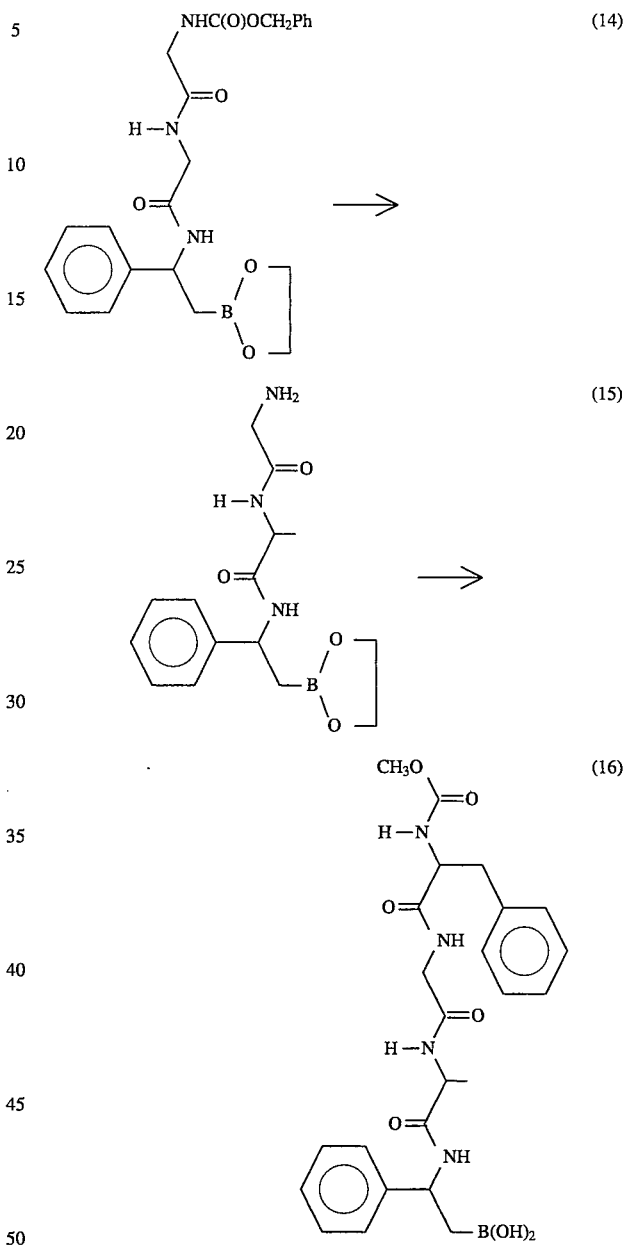

Compound (14) is prepared by mixing ethylene glycol (0.17 g, 2.7 mmoles) with the boronic acid (13) (1.06 g, 2.5 mmoles) in methylene chloride (10 ml) by a procedure previously described (see Examples V and VI). The ester, compound (14) (1.07 g, 2.4 mmoles) is dissolved in methanol (60 ml) and placed in a pressure vessel. To the vessel is added 10% Palladium on carbon (0.21 g) and the vessel is agitated under 50 psi hydrogen for 3 hours at room temperature. After this, the catalyst is removed by filtration and the solvent by heating under reduced pressure. The residue is purified by silica gel chromatography to afford compound (15). Compound (16) is prepared by the sequential addition of compound (15) (0.65 g, 2.0 mmoles) dissolved in dichloromethane (5 ml), N-MOC-Phe (0.48 g, 2.2 mmoles) dissolved in dichloromethane (5 ml), and triethylamine (0.52 g, 5.15 mmoles) also dissolved in dichloromethane (5 ml) to a 100 ml round bottom flask containing dichloromethane (50 ml), and fitted with a gas inlet and a septum. While constantly stirring this solution at room temperature under an inert atmosphere, diethylcyanophosphonate (0.42 g, 2.6 mmoles) is added slowly. The reaction is stirred overnight. After removing the volatiles under reduced pressure, the residue is dissolved in ethyl acetate (30 ml) and extracted with one portion (15 ml) of 2N HCl in a separatory funnel. The funnel is shaken for 12 minutes until compound (16) precipitates and is suspended in the aqueous layer. Compound (16) is collected by filtration and dried under vacuum.

EXAMPLE VII

A liquid laundry detergent base matrix is prepared as follows:

| Ingredients | % By Weight |
|---|---|
| $C_{14-15}$ alkyl polyethoxylate (2.25) sulfonic acid | 8.43 |
| $C_{12-13}$ alkyl ethoxylate | 3.37 |
| $C_{12.3}$ linear alkylbenzene sulfonic acid | 8.43 |
| Dodecyl trimethyl ammonium chloride | 0.51 |
| Sodium tartrate mono-and di-succinate (80:20 mix) | 3.37 |
| Citric acid | 3.37 |
| $C_{12-14}$ fatty acid | 2.95 |
| Tetraethylene pentaamine ethyxylate (15–18) | 1.48 |
| Ethoxylated copolymer of polyethylene -polypropylene terephthalate polysulfonic acid | 0.20 |
| Brightener | 0.10 |
| Ethanol | 1.47 |
| Monoethanolamine | 1.05 |
| Sodium formate | 0.32 |
| 1,2 propane diol | 6.00 |
| Sodium hydroxide | 2.10 |
| Silicone suds suppressor | 0.0375 |
| Sodium cumene sulfonate | 3.00 |
| Lipase (100 KLU/g) | 0.49 |
| Ingredients per Examples I–III | 1.00 |
| Water/miscellaneous | 52.3225 |
| Total | 100.00 |
| pH (10% solution) | 8.2–8.5 |

The base matrix is then used in the formulations shown below.

| | % By Weight | | |
|---|---|---|---|
| | Example 1 | Example 2 | Example 3 |
| Base matrix 1 | 99.0 | 99.0 | 99.0 |
| 2-N-[Ala—CBZ]-2-phenylethane-aminoboronic acid | 0.2 | | |
| 2-N-[Ala—Gly—CBZ]-amino-2-phenyl-ethaneboronic acid | | 0.2 | |
| 2-N-[Ala—Gly—MOC]-amino-2-phenyl-ethaneboronic acid | | | 0.2 |
| Protease B | 0.5 | 0.5 | 0.5 |
| Water | 0.3 | 0.3 | 0.3 |
| | 100.0 | 100.0 | 100.0 |
| pH (10% solution) | 7.9–8.2 | 7.9–8.2 | 7.9–8.2 |

What is claimed is:

1. A composition which has serine protease reversible inhibition properties and which is useful for incorporation into enzyme-containing liquid detergent products, which composition comprises a serine protease and an effective amount of a protease inhibitor compound having the formula:

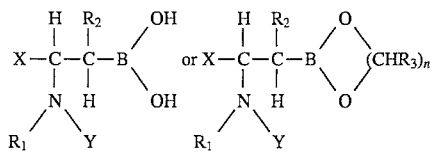

where $R_1$, $R_2$, and $R_3$ are independently hydrogen or $C_1$–$C_4$ alkyl; n is 2–4; X is phenyl or $C_1$–$C_6$ alkyl; and Y is selected from the group consisting of
(a) hydrogen;
(b) an amine protecting group selected from the group consisting of
  i) t-butoxycarbonyl,
  ii) methoxycarbonyl,
  iii) benzyloxycarbonyl, and

wherein $R_5$ is phenyl or $C_1$–$C_4$ alkyl; and
iv)
(c)

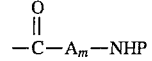

wherein A is independently selected from naturally occurring amino acids; m is 1 to 3; and P is selected from the protecting groups of Component (b).

2. A composition according to claim 1 where the protease inhibitor compound has the following structure:

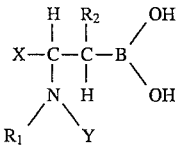

where $R_1$ and $R_2$ are independently hydrogen or methyl; X is phenyl or $C_1$–$C_4$ alkyl; and Y is an amine protecting group selected from the group consisting of t-butoxycarbonyl, methoxycarbonyl, benzyloxycarbonyl, and

where $R_5$ is phenyl or $C_1$–$C_4$ alkyl.

3. A composition according to claim 1 wherein the protease inhibitor compound has the following structure:

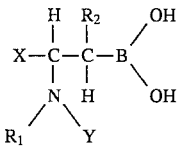

where $R_1$ and $R_2$ are each hydrogen or methyl; X is phenyl or $C_1$–$C_4$ alkyl; and Y is

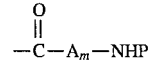

where A is independently selected from naturally occurring amino acids, m=1–2, and P is hydrogen or an amine protecting group selected from the group consisting of t-butoxycarbonyl, methoxycarbonyl, benzyloxycarbonyl, and

where $R_5$ is phenyl or $C_1$–$C_4$ alkyl.

4. A composition according to claim 1 wherein the protease inhibitor compound has the following structure:

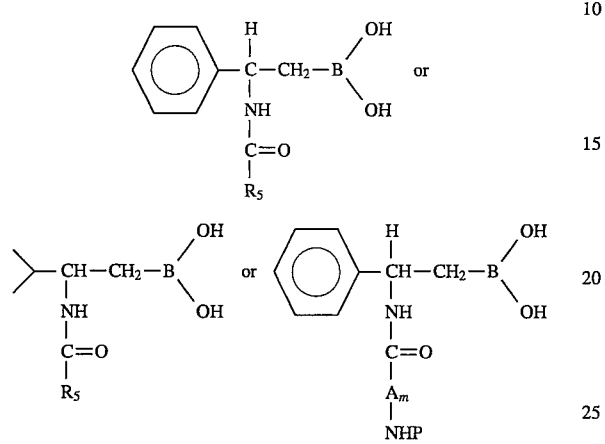

where $R_5$ is phenyl or $C_1$–$C_4$ alkyl; m=1–3; A is independently selected from the group consisting of alanine, valine, leucine, phenylalanine, glycine, isoleucine and threonine; and P is selected from the group consisting of t-butoxycarbonyl, methoxycarbonly, benzyloxycarbonyl, and

5. A composition according to claim 4 wherein the protease inhibitor compound has the following structure:

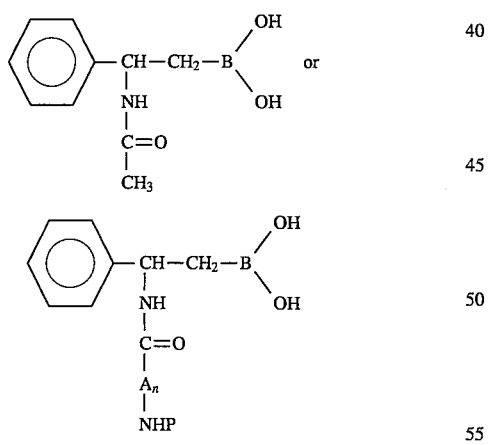

where n=2–4; A is independently selected from the group consisting of alanine, glycine, leucine, valine and phenylalanine; and P is selected from the group consisting of t-butoxycarbonyl, methoxycarbonyl, benzyloxycarbonyl, and

6. A method for reversibly inhibiting the activity of serine protease, which method comprises the steps of:

I) mixing into a liquid medium from about 0.001% to about 10% by weight of a protease inhibitor compound of the formula:

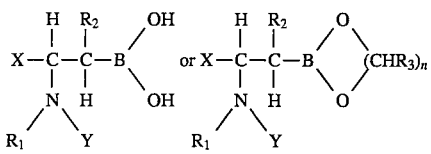

wherein $R_1$, $R_2$, and $R_3$ are independently hydrogen or $C_1$–$C_4$ alkyl; n is 2–4; X is phenyl or $C_1$–$C_6$ alkyl; and Y is selected from the group consisting of
(a) hydrogen;
(b) methoxycarbonyl,
  i) t-butoxycarbonyl,
  ii) methoxycarbonyl,
  iii) benzyloxycarbonyl, and
  iv)

wherein $R_5$ is phenyl or $C_1$–$C_4$ alkyl; and
(c)

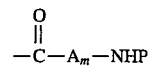

wherein A is independently selected from naturally occurring amino acids; m is 1 to 3; and P is selected from the amine protecting groups of Component(b); and II) mixing into the same liquid medium from about 0.0001% to about 10% by weight of active enzyme of serine protease.

7. A method according to claim 6 wherein the protease inhibitor compound has the following structure:

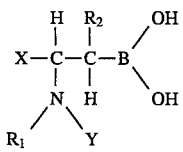

wherein $R_1$ and $R_2$ are independently hydrogen or methyl; X is phenyl or $C_1$–$C_4$; and Y is an amine protecting group selected from the group consisting of t-butoxycarbonyl, methoxycarbonyl, benzyloxycarbonyl, and

where $R_5$ is phenyl or $C_1$–$C_4$ alkyl.

8. A method according to claim 6 wherein the protease inhibitor compound has the following structure:

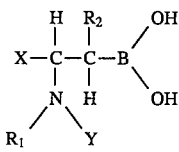

where $R_1$ and $R_2$ are each hydrogen or methyl; X is phenyl or C1–C4 alkyl; and Y is

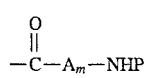

where A is independently selected from naturally occurring amino acids, m=1–2, and P is hydrogen or an amine protecting group selected from the group consisting of t-butoxycarbonyl, methoxycarbonyl, benzyloxycarbonyl, and

where $R_5$ is phenyl or $C_1$–$C_4$ alkyl.

9. A method according to claim 6 wherein the protease inhibitor compound has the following structure:

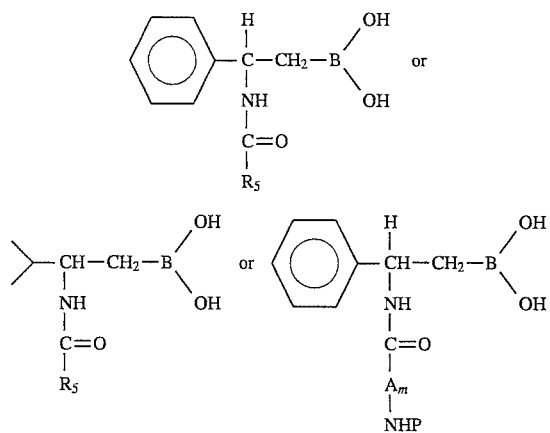

wherein $R_5$ is phenyl or $C_1$–$C_4$ alkyl; m=1–3; A is independently selected from the group consisting of alanine, valine, leucine, phenylalanine, glycine, isoleucine and threonine; and P is selected from the group consisting of t-butoxycarbonyl, methoxycarbonyl, benzyloxycarbonyl, and

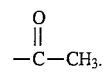

10. A method according to claim 9 wherein the protease inhibitor compound has the following structure:

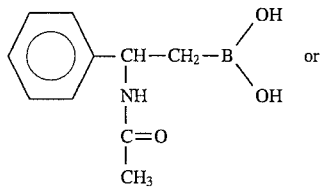

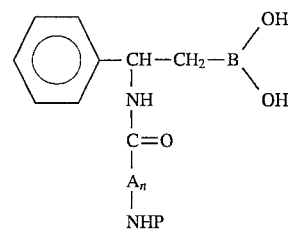

where n=2–4; A is independently selected from the group consisting of alanine, glycine, leucine, valine, and phenylalanine; and P is selected from the group consisting of t-butoxycarbonyl, methoxycarbonyl, benzyloxycarbonyl, and

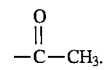

* * * * *